United States Patent
Kandori et al.

(10) Patent No.: US 6,665,553 B2
(45) Date of Patent: Dec. 16, 2003

(54) BIOMAGNETIC FIELD MEASURING APPARATUS USING SQUID MAGNETOMETERS FOR EVALUATING A ROTATIONAL PROPERTY OF A CURRENT IN A SUBJECT

(75) Inventors: Akihiko Kandori, Kokubunji (JP); Tsuyoshi Miyashita, Fuchu (JP); Keiji Tsukada, Kashiwa (JP); Masahiro Murakami, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/120,406

(22) Filed: Apr. 12, 2002

(65) Prior Publication Data

US 2002/0158631 A1 Oct. 31, 2002

(30) Foreign Application Priority Data

Apr. 27, 2001 (JP) .......................... 2001-130604

(51) Int. Cl.[7] ................................. A61B 5/05
(52) U.S. Cl. ................. 600/409; 324/244; 324/248
(58) Field of Search .................. 600/409; 324/244, 324/248

(56) References Cited

U.S. PATENT DOCUMENTS

| | | | | |
|---|---|---|---|---|
| 5,152,288 A | * | 10/1992 | Hoenig et al. | 600/409 |
| 5,285,385 A | * | 2/1994 | Igarashi et al. | 600/409 |
| 6,230,037 B1 | * | 5/2001 | Tsukada et al. | 600/409 |
| 6,370,414 B1 | * | 4/2002 | Robinson | 600/409 |
| 6,374,131 B1 | * | 4/2002 | Tomita et al. | 600/409 |
| 6,522,908 B1 | * | 2/2003 | Miyashita et al. | 600/409 |
| 2001/0009975 A1 | * | 7/2001 | Tsukada et al. | 600/409 |
| 2002/0062076 A1 | * | 5/2002 | Kandori et al. | 600/409 |
| 2002/0115927 A1 | * | 8/2002 | Tsukada et al. | 600/409 |

* cited by examiner

Primary Examiner—Francis J. Jaworski
Assistant Examiner—Runa Shah Qaderi
(74) Attorney, Agent, or Firm—Antonelli, Terry, Stout & Kraus, LLP

(57) ABSTRACT

A biomagnetic field measuring apparatus including: a plurality of magnetometers each employing a superconducting quantum interference device for measuring the magnetic field generated from an organism; a unit for calculating a pseudo-current from a normal component of the magnetic field; a unit for calculating the pseudo-current from the magnetic field obtained from the plurality of magnetometers to integrate the pseudo-current in a fixed direction on the circumference at a fixed distance from each of the associated ones of the sensors; a unit for calculating a maximum value or a minimum value of the integral value obtained by the unit for performing the integral; and a unit for calculating a difference value between the absolute value of the maximum value and the absolute value of the minimum value.

3 Claims, 10 Drawing Sheets

MEASUREMENT AREA OF
LEFT TEMPORAL LOBE

MEASUREMENT AREA OF
RIGHT TEMPORAL LOBE (a)

(b)

502 SUMMATION AREA (c)

DIRECTION OF SUMMATION $I_{rot} = I_1 + I_2 + I_3 + I_4$

MEASUREMENT OF
RIGHT TEMPORAL LOBE

LEFT EAR
SIMULI

801

BIOMAGNETIC FIELD MEASURING APPARATUS USING SQUID MAGNETOMETERS FOR EVALUATING A ROTATIONAL PROPERTY OF A CURRENT IN A SUBJECT

BACKGROUND OF THE INVENTION

The present invention relates in general to a biomagnetic field measuring apparatus using SQUID (Superconducting Quantum Interference Device) magnetometers for measuring a weak magnetic field generated from the heart, the brain or the like of an adult, a child, an unborn baby or a fetus, or the like. In particular, the invention relates to a method of evaluating the rotational property of a current in the heart or the brain on the basis of the distribution of the measured magnetoencephalogram and the measured magnetocardiogram.

Heretofore, a biomagnetic field measuring apparatus employing SQUID magnetometers has been used in the measurement of a weak biomagnetic field (the measured magnetic field is called the magnetocardiogram or the magnetoencephalogram) which is caused by an ion current generated along with the myocardial electric activity within an organism (generality of the muscle activity) or the activity of neurons in the brain. The motion of the ion current reflects the electric activity of an organism. Thus, the useful information can be obtained from the motion of an ion current and hence many studies are being made. As a method of observing a pseudo-current within the heart from these measured magnetic fields, the current-arrow map method has been proposed (Medical & Biological Engineering & Computing 2001, Vol. 39, pp. 21–28). The calculation for the current-arrow map method is obtained by differentiating partially the magnetic field in a normal component (i.e., the magnetic field in a direction intersecting perpendicularly an organism) with respect a tangential component (i.e., a direction parallel with an organism). Thus, the pseudo-current in the inside of the heart can be estimated by utilizing the current-arrow map method, and thus the effectiveness of the current-arrow map method has been shown.

However, the method of evaluating quantitatively a rotating current within the brain or the heart is not considered, and hence it is impossible to obtain the information which can be sufficiently clinically evaluated.

SUMMARY OF THE INVENTION

In the light of the foregoing, the present invention has been made in order to solve the above-mentioned problem associated with the prior art, and it is therefore an object of the present invention to provide a method of evaluating quantitatively the rotational property of a current within the brain or the heart on the basis of the magnetic field waveform which is obtained by using a biomagnetic field measuring apparatus for measuring a weak magnetic field generated from the brain or the heart.

In order to attain the above-mentioned object, according to the present invention, there is provided a biomagnetic field measuring apparatus including: a plurality of magnetometers each employing a superconducting quantum interference device (hereinafter, referred to as an SQUID for short, when applicable) for measuring a magnetic field generated from an organism; a unit for calculating a pseudo-current on the basis of the measured magnetic field; a unit for calculating the pseudo-current on the basis of the magnetic field obtained by the plurality of magnetometers to integrate the pseudo-current in a fixed direction on a circumference which is a fixed distance away from each of the sensors; a unit for calculating a maximum value or a minimum value of the integral value obtained by the unit for carrying out the integration; and a unit for calculating a difference value between the absolute value of the maximum value and the absolute value of the minimum value.

According to the present invention having the above-mentioned construction, it is possible to obtain easily the information useful in the quantitative evaluation of the rotational property on the basis of the magnetic field distribution having the rotating current in patients with dizziness, patients with atrial flutter or the like.

As described above, according to the present invention having the above-mentioned construction, it is possible to obtain an index useful in the diagnosis.

DESCRIPTION OF THE EMBODIMENTS

The embodiments of the present invention will hereinafter be described in detail with reference to the accompanying drawings.

An embodiment will now be described.

Figure 1:
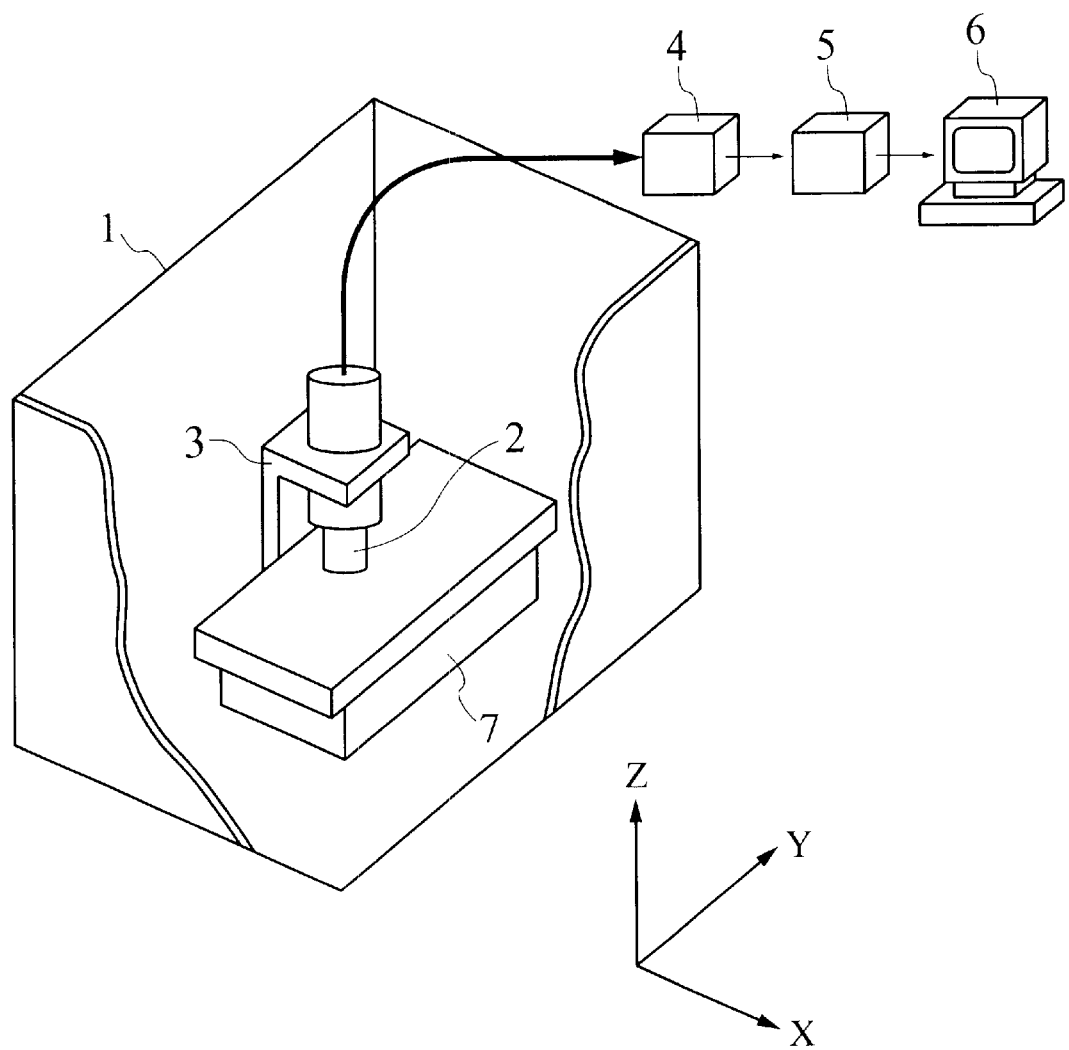
FIG. 1 is a schematic view showing construction of a biomagnetic field measuring apparatus.

FIG. 1 is a schematic view showing construction of a biomagnetic field measuring apparatus as an embodiment of the present invention. A bed 7 on which a subject to be tested lies down, a cryostat 2 in which coolant (liquid helium or liquid nitrogen) for holding SQUID sensors in a superconducting state is stored, and a gantry 3 for holding mechanically the cryostat 2 are arranged within a magnetically shielded room 1 as shown in FIG. 1. The bed can be moved in X, Y and Z directions. A driving circuit 4 for driving the SQUID magnetometers, an amplifier and filter unit 5, a computer 6 for data acquisition are arranged in the outside of the magnetically shielded room 1. In the present embodiment, the computer 6, for data acquisition serves also as a display unit for displaying thereon the analyzed data, and an analysis unit for analyzing the acquired data.

Figure 2:
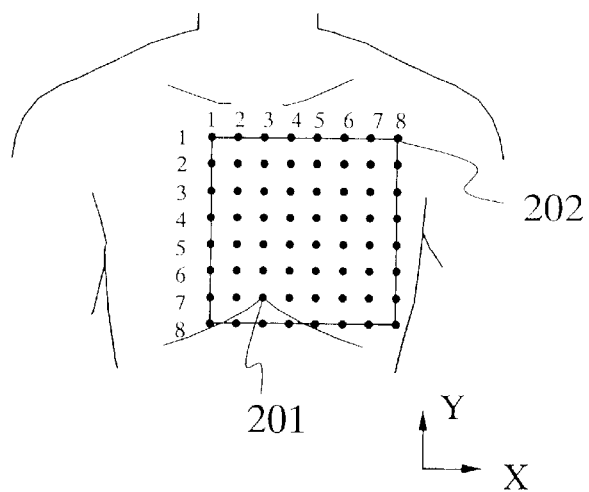
FIG. 2 is a schematic view showing the arrangement of 64 SQUID magnetometers which are arranged in an array of 8×8.

FIG. 2 shows the arrangement of 64 SQUID magnetometers 202, arranged in an array of, 8×8, for measuring a weak magnetic field generated from the heart. In the present embodiment, the magnetometer which uses a first order gradiometer having a pickup coil and a compensation coil and in which the pickup coil is adapted to measure the magnetic field in a Z-direction (i.e., in the direction perpendicular to the surface of the body) is defined as the SQUID magnetometer. But, the shape of the pickup coil is not intended to be limited to the pickup-coil for measuring the magnetic field in the Z-direction. In the figure of the present embodiment, the SQUID magnetometer 202 is used in which the baseline of the first order gradiometer is set to 50 mm and the diameter of the pickup coil is set to 18 mm. The alignment between the measurement area of the heart of an adult and the heart thereof is carried out by aligning the SQUID magnetometer 201 at a position (3, 7) above a xiphisternum. While in the present embodiment, the sensor array is shown in the form of a square array in which the 64 SQUID magnetometers 202 are arranged in an array of 8×8, alternatively, the sensor array having a triangular arrangement or a rhomboid arrangement may also be employed for the measurement. Also, the direction of the magnetic field to be measured is not intended to be limited to the Z-direction. That is, the magnetic field may also be detected in an arbitrary direction of three components of the vector of the magnetic field.

The biomagnetic field measuring apparatus according to the present invention includes: a bed for holding a subject to be tested; a plurality of magnetometers for measuring the biomagnetic field generated from the subject to be tested; a cryostat for holding a plurality of magnetometers at a low temperature; a holding unit for holding the cryostat; a magnetometer operating circuit for driving a plurality of magnetometers; an arithmetic operation unit (computer) for collecting output signals from the magnetometer operating circuit in the form of digital magnetic field signals to operate arithmetically these magnetic field signals; and a display unit for displaying thereon the arithmetic processing result.

A plurality of magnetometers have the pickup coils which are arranged two-dimensionally on a plane (it is decided as an xy plane) so as to be adjacent to the measurement part of the magnetocardiogram, and a superconducting quantum interference devices for converting the magnetic field (in the present embodiment, it is assumed that a component Bz in the normal direction of the magnetocardiogram is detected) detected by the pickup coils into an electric signals. Thus, the magnetocardiogram which is generated from a subject to be tested are collected in the form of the digital magnetic field signals at a plurality of positions (x, y) where a plurality of magnetometers are arranged two-dimensionally through the magnetometers arranged two-dimensionally.

The arithmetic operation unit executes (1) the arithmetic operation process for differentiating partially the magnetic field signals collected as described above with respect to each of the x and y directions to obtain the pseudo-current, and (2) the arithmetic operation process for integrating curvilinearly (i.e., adding) discretely a component of the pseudo-current contacting a circumference (a tangential component of the pseudo-current) on that circumference, which is an arbitrary fixed distance away from a predetermined position (measurement point) (x, y), within the area (measurement area), in which a plurality of magnetometers are arranged, in a fixed direction from an arbitrary position on the circumference to obtain an integral value (i.e., an addition value).

In addition, the arithmetic operation unit executes the arithmetic operation process for obtaining a minimum value and a maximum value of the integral value (i.e., the addition value) obtained through the arithmetic operation process (2), and the arithmetic operation process for obtaining a difference value between the absolute value of that minimum value and the absolute value of that maximum value. At least any one of the minimum value of that integral value (i.e., that addition value), the maximum value of that integral value, and the difference value between the above-mentioned absolute values is displayed on the display unit.

Furthermore, the arithmetic operation unit executes the arithmetic operation process for obtaining the above-mentioned integral values (i.e., the addition values) in all of the measurement points (x, y) and also the arithmetic operation process for obtaining contour lines each connecting the equal integral values (i.e., the equal addition values). The resultant contour lines are displayed on the display unit.

While in the above-mentioned description, a plurality of magnetometers are arranged two-dimensionally on a plane so as to be adjacent to the measurement part (the breast or the head) of the magnetocardiogram, in the case where the measurement part of the magnetocardiogram is the head, a plurality of magnetometers may also be arranged on the spherical surface having a radius slightly larger than that of the sphere by which the outer shape of the head is approximated to detect a normal component of the magnetoencephalogram.

In the present invention, the normal component of either the magnetocardiogram generated from the heart or the magnetoencephalogram is detected to execute the above-mentioned arithmetic operation processes, whereby the information useful in the diagnosis of an organism is obtained through the simple arithmetic operation processes.

Figure 3:
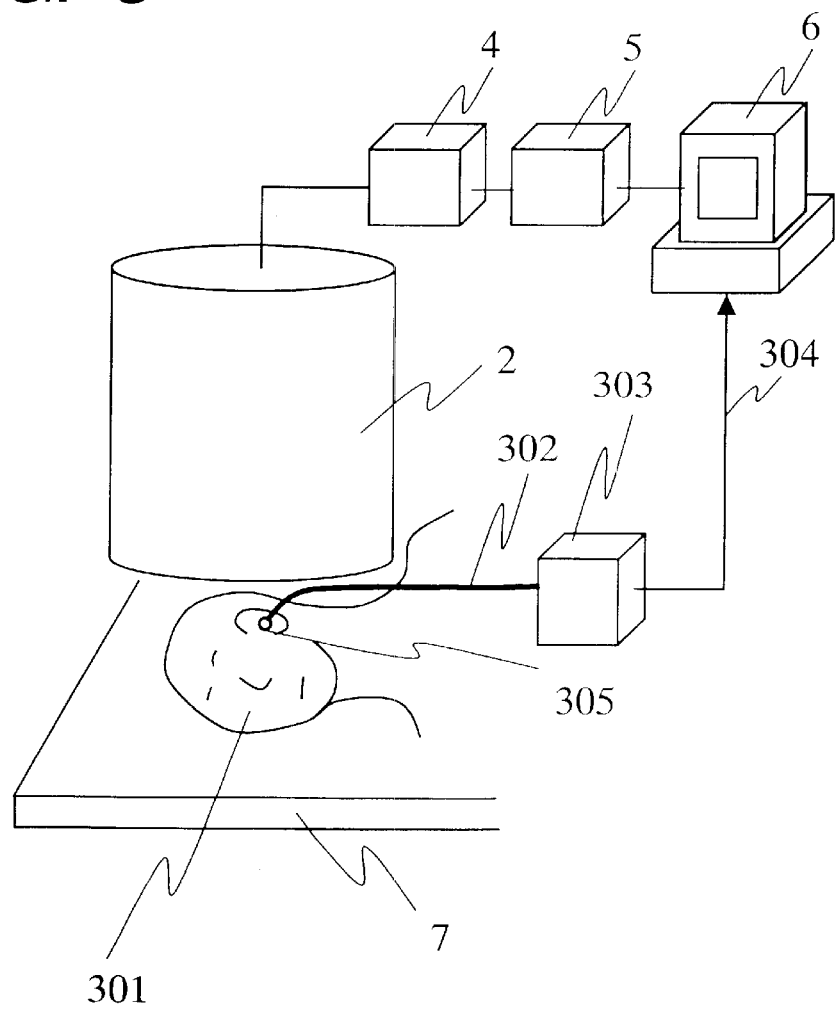
FIG. 3 is a schematic view showing an example of measuring an auditory evoked magnetic field.

FIG. 3 is a schematic view showing construction of a system for measuring the magnetic field generated through the neural activity of the brain (hereinafter, referred to as "the magnetoencephalogram" for short, when applicable). In the present embodiment, there is shown an example of measuring the auditory evoked magnetic field generated due to the sound stimulation. A subject to be tested lies down on the bed 7 and brings his/her face of the head wanted to be measured close to the cryostat 2 to measure the magnetoencephalogram. In FIG. 3, the tone-burst sound having a holding time width of 50 msec. at 1 kHz is generated by a sound stimulator 303. The sound stimulation is given at intervals of about 3.3 sec. (corresponding to 0.3 Hz). A synchronous signal 304 is generated synchronously with the timing of the sound stimulation to be inputted to the computer 6 for data acquisition. The averaging process is executed by utilizing the inputted synchronous signal to enhance the signal-to-noise ratio. The tone-burst sound which has been generated by the sound stimulator 303 is inputted to an left ear of the subject through an air tube 302 and an adapter 305. In addition, while not illustrated in FIG. 3, the measurement is carried out in such a way that the sound of the white noise is supplied to a right ear of the subject at all times to remove the influence of any of the sounds coming from the outside. The magnetoencephalogram is measured by the SQUID magnetometers provided within the cryostat 2. The SQUID magnetometers are driven by an FLL (Flux Locked Loop) circuit 4 and an output signal from the FLL circuit 4 is recorded in the form of digital data in the computer 6 for data acquisition through the amplifier and filter circuit 5. The control screen, the data analysis screen and the like of the computer 6 for data acquisition, the FLL circuit 4, the amplifier and filter circuit 5 and the like are all displayed on the computer 6 for data acquisition. In the above-mentioned construction, it is desirable to arrange the constituent elements other than the bed 7 and the cryostat 2 in the outside of the magnetically shielded room 1 shown in FIG. 1.

Figure 4:
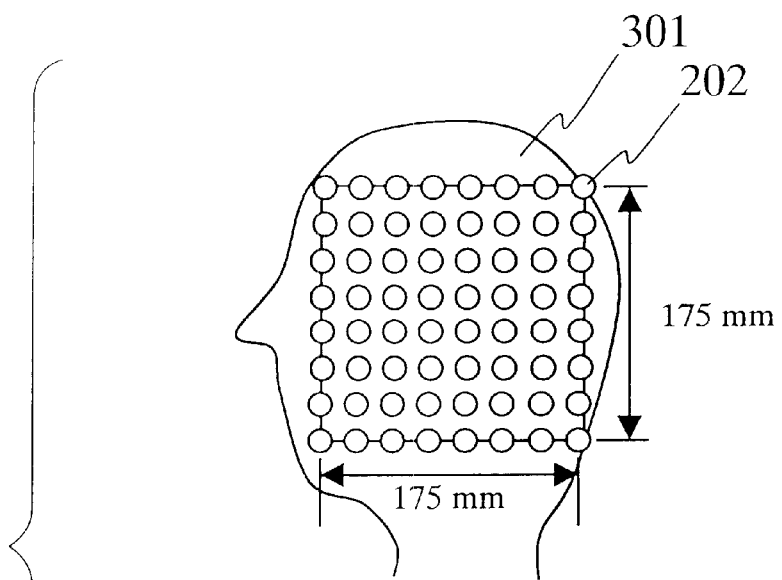
FIG. 4 is a schematic view showing a measurement area of the magnetoencephalogram measurement.
Figure 4:
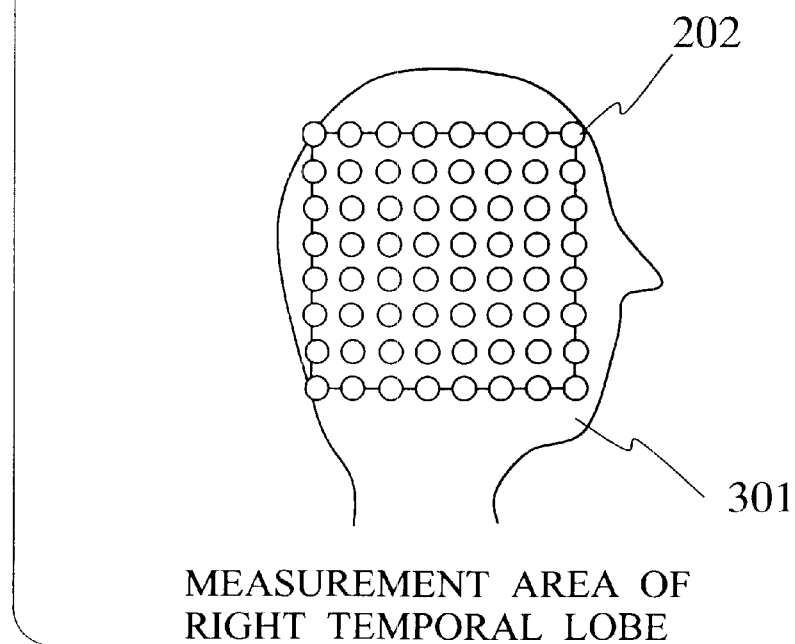

Referring now to FIG. 4, the measurement area (175 mm×175 mm) in each of the areas to be measured is illustrated using measurement points 202. In the figure, a upper stage shows the measurement area when the left temporal head of a subject 301 to be tested is measured, and a lower stage shows the measurement area when the right temporal head thereof is measured. Since FIG. 4 shows the arrangement when the auditory evoked magnetic field is measured, some measurement points 202 are arranged slightly above each of ears.

In order to examine the electric activity within the brain by applying the acoustic stimulation, we used the current-arrows map method. The current-arrow map method is the method wherein the magnetic field (Bz) in the Z-direction perpendicular to the body is partially differentiated in the x and y directions to make the pseudo-current visible. More specifically, the partial differential is expressed by the following Expressions.

$$Ix = dBz/dy \quad (1)$$

$$Iy = -dBz/dx \quad (2)$$

Figure 5:
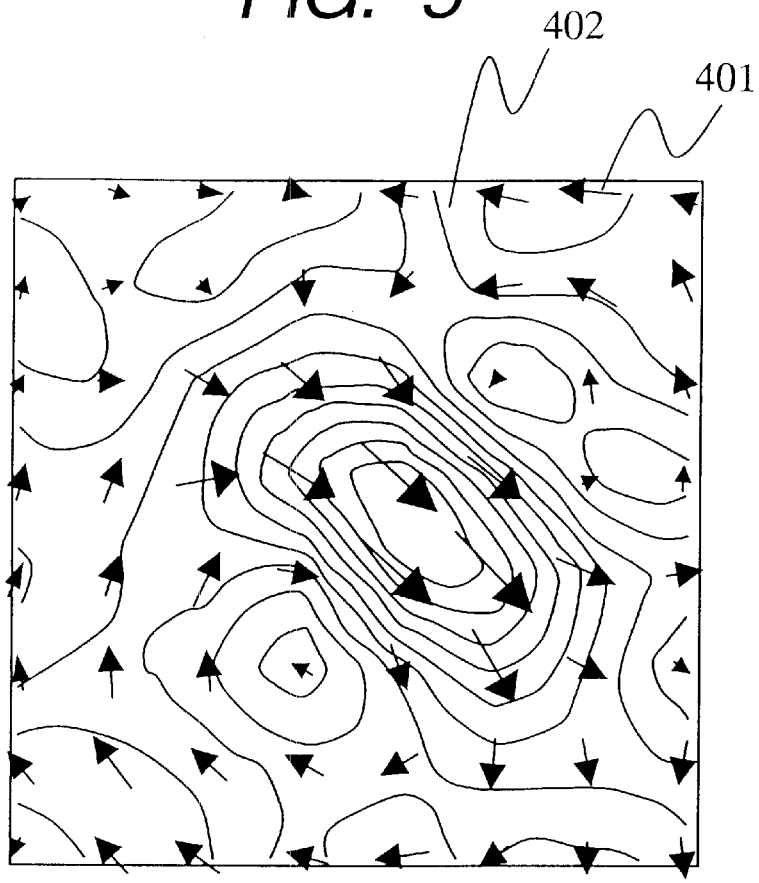
FIG. 5 is a schematic diagram showing an example of measuring an auditory evoked magnetic field of a healthy subject in which a upper stage is a current-arrow map diagram and a lower stage is overlapping waveforms of 64 channel magnetoencephalograms.
Figure 5:
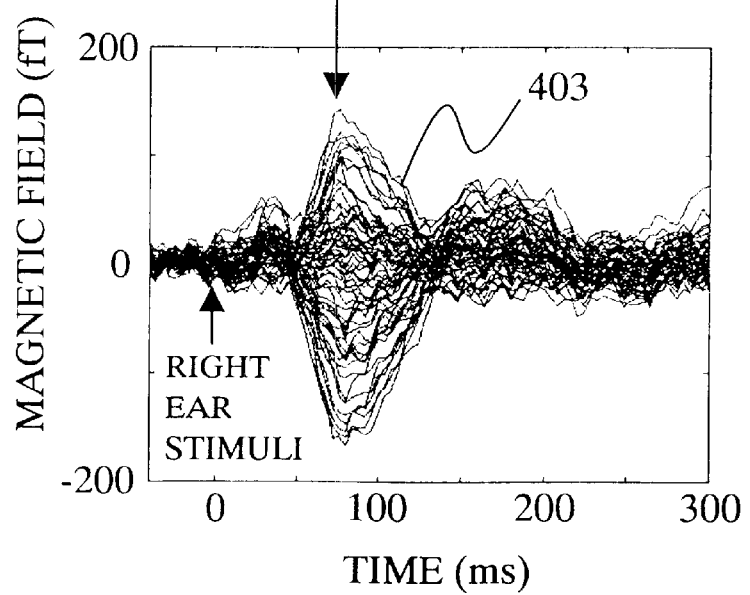

Now, Ix and Iy are referred to as current arrows and it is considered that each of the current arrows exhibits a pseudo-current. FIG. 5 shows a magnetic field waveform 403 which is measured in the left temporal head when the tone-burst sound is inputted to a right ear of a healthy subject. Then, a upper stage of FIG. 5 shows a current-arrow map diagram which is produced using Expressions (1) and (2) at a time (N100) when the magnitude of the magnetic field waveform 403 is largest. Arrows 401 at the upper stage show the difference in intensity in the form of lengths of arrows, and a contour map 402 represents the same intensities of the current arrows 401. By the way, the expression form of the above-mentioned pseudo-current is intended to be limited to the current arrow produced by utilizing the current-arrow map method. For example, there may be adopted the current vectors of the two- or three-dimensional current distribution which are obtained by utilizing the reconstruction method of two- or three-dimensional current distribution employing the Fourier transform method or the reconstruction method of two- or three-dimensional current distribution based on the inverse matrix of lead field matrix. Then, in the case of the three-dimensional current distribution, the current vectors can be expressed within an arbitrary two-dimensional current distribution. But, the following description will be given on the basis of the current arrows employing the current-arrow map method and calculated from Expressions (1) and (2).

Figure 6:
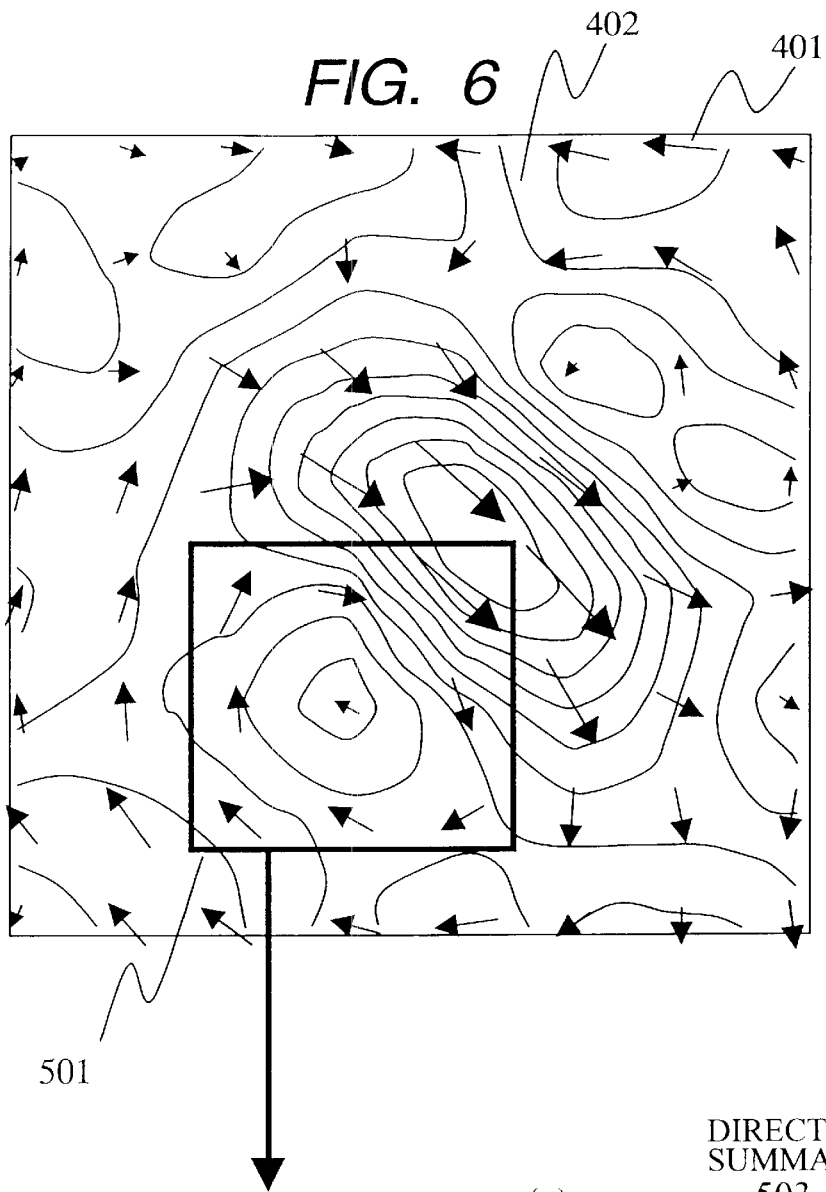
FIG. 6 is a schematic diagram showing a method of producing rotation current arrows.
Figure 6:
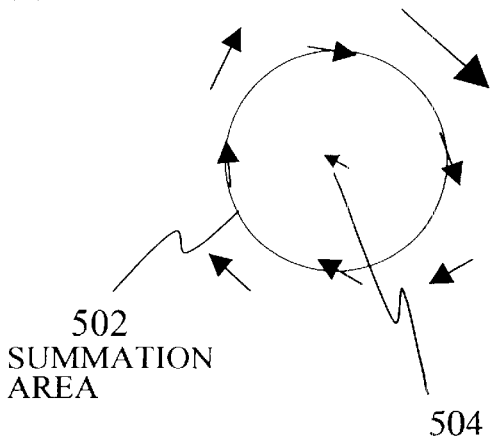
Figure 6:
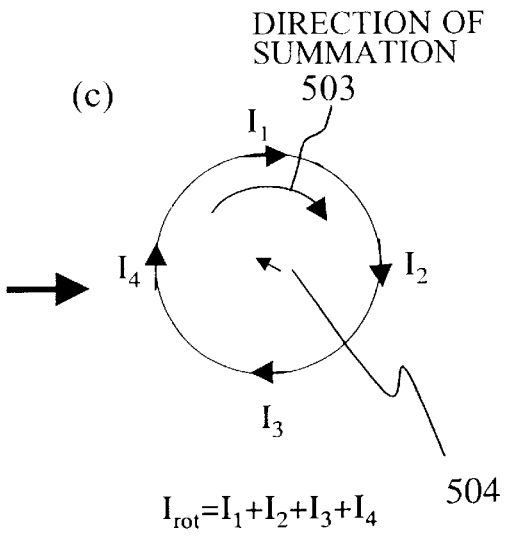

In order to confirm the rotational property of the current arrows, we have studied the rotation current arrow (Irot). The rotation current arrow (Irot) will now be described with reference to FIG. 6. FIG. 6(a) shows a current-arrow map similar to that shown in the upper stage of FIG. 5. For the sake of simplicity of the description, only the current arrows extracted from an area 501 are shown in FIG. 6(b). With respect to a rotation current arrow 504 at the center (channel) within FIG. 6(b), the curvilinear integral is carried out for a summation area 502 having a circumference which is an equal distance away from the center current arrow 504. FIG. 6(c) shows the situation in which only current-arrow components 11, 12, 13 and 14 each contacting the circumference of the summation area 502 are curvilinearly integrated along a direction 503 of summation. Since the direction of summation is decided as plus, in the example shown in FIG. 6(c), the value of Irot=I1+I2+I3+I4 has a plus value, and hence it is possible to be aware of the presence of the current arrows rotating in a clockwise direction around the center current arrow 504. Likewise, the rotation current arrow (Irot) is calculated every sensor (channel). But, since the calculation can not be carried out with respect to the sensors, located in the most peripheral positions, of the sensors arranged in a matrix of 8×8, we calculated the rotation current arrow (Irot) with respect to each of the inner sensors arranged in 6×6. While the current-arrow map method employing Expressions (1) and (2) is used in the calculation of the above-mentioned rotation current arrow (Irot), the present invention is not intended to be limited thereto. For example, there may also be adopted a current vector of two-dimensional current distribution corresponding to the inverse problem and obtained by utilizing the reconstruction method of two-dimensional current distribution employing the Fourier transform method or the reconstruction method of two-dimensional current distribution based on the inverse matrix of lead field matrix. Furthermore, the summation area of the rotation current arrow (Irot) is also not intended to be limited to the four-place currents (I1, I2, I3 and I4) shown in FIG. 6(c). That is, it is also possible that the current-arrow map is produced by calculating interpolation values of the magnetic field between the sensors to sum up a plurality of current arrows, thereby calculating the rotation current arrow (Irot).

Figure 7:
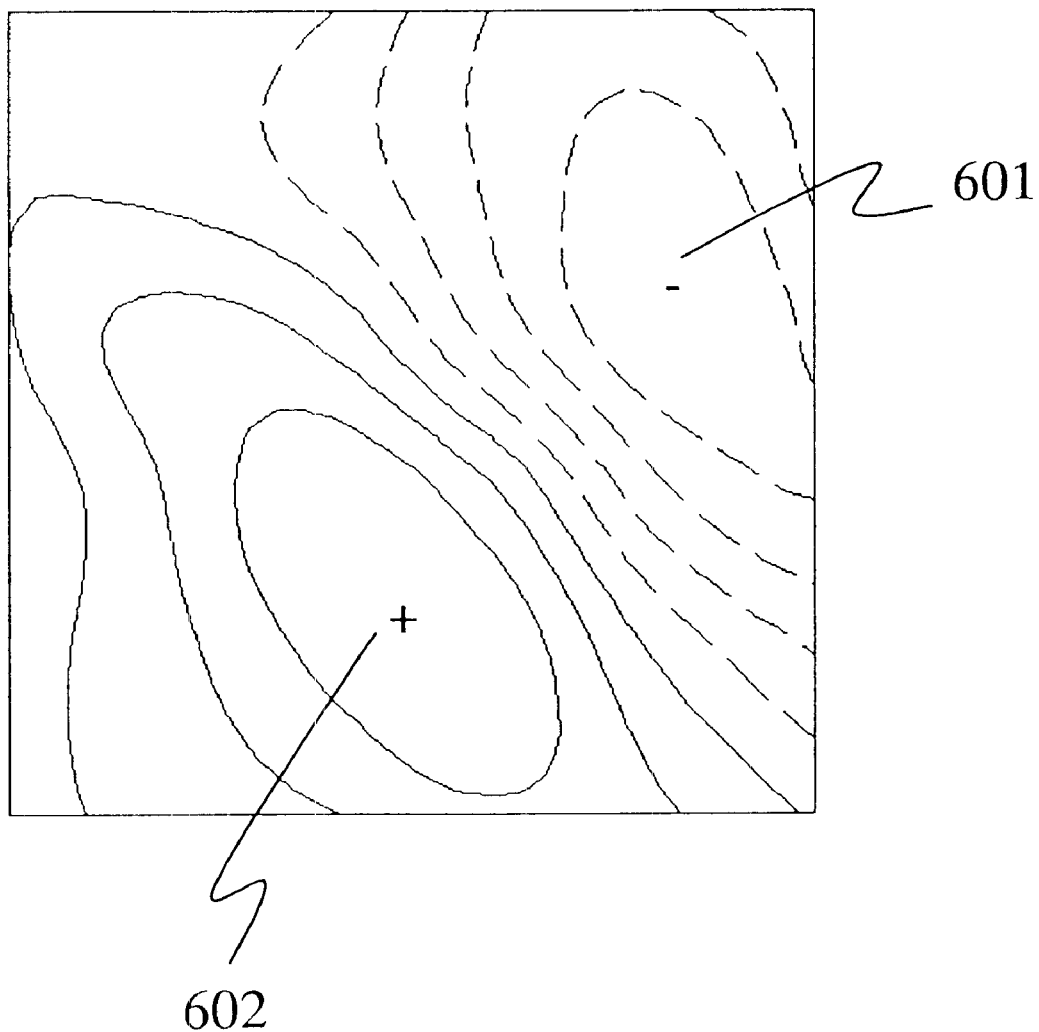
FIG. 7 is a map diagram based on rotation current arrows of a healthy subject.

FIG. 7 shows a map diagram of the rotation current arrow (Irot) which is calculated from the current-arrow map diagram shown in FIG. 6(a). As shown in FIG. 7, a positive peak 602 and a negative peak 601 having roughly the same magnitude appear on the both sides of the sensor having the maximum current arrow value within FIG. 6(a).

Figure 8:
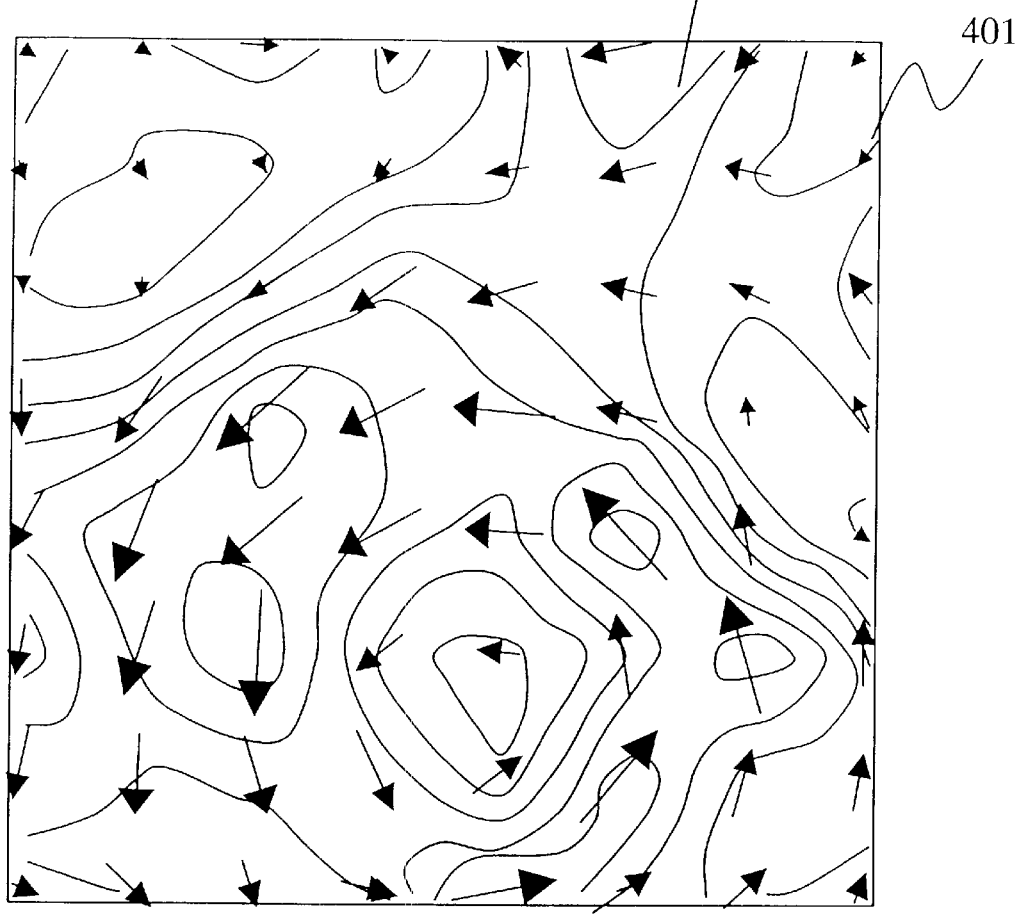
FIG. 8 is a schematic diagram showing an example of measuring an auditory evoked magnetic field of patients with dizziness in which a upper stage is a current-arrow map diagram and a lower stage is overlapping waveforms of 64 channel magnetoencephalograms.
Figure 8:
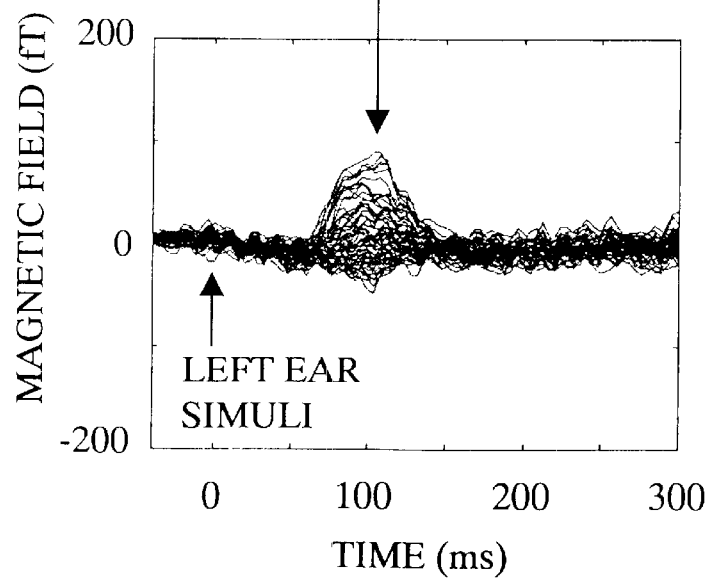

Next, magnetic waveforms 701 detected in the right temporal head by applying stimuli to a left ear of a patient with dizziness are shown in a lower stage of FIG. 8, and a current-arrow map diagram when the magnetic field waveforms 701 are at the maximum peaks is shown in a upper stage of FIG. 8. The situation in which the current arrows are rotated can be observed from the current-arrow map diagram in the upper stage of FIG. 8.

Figure 9:
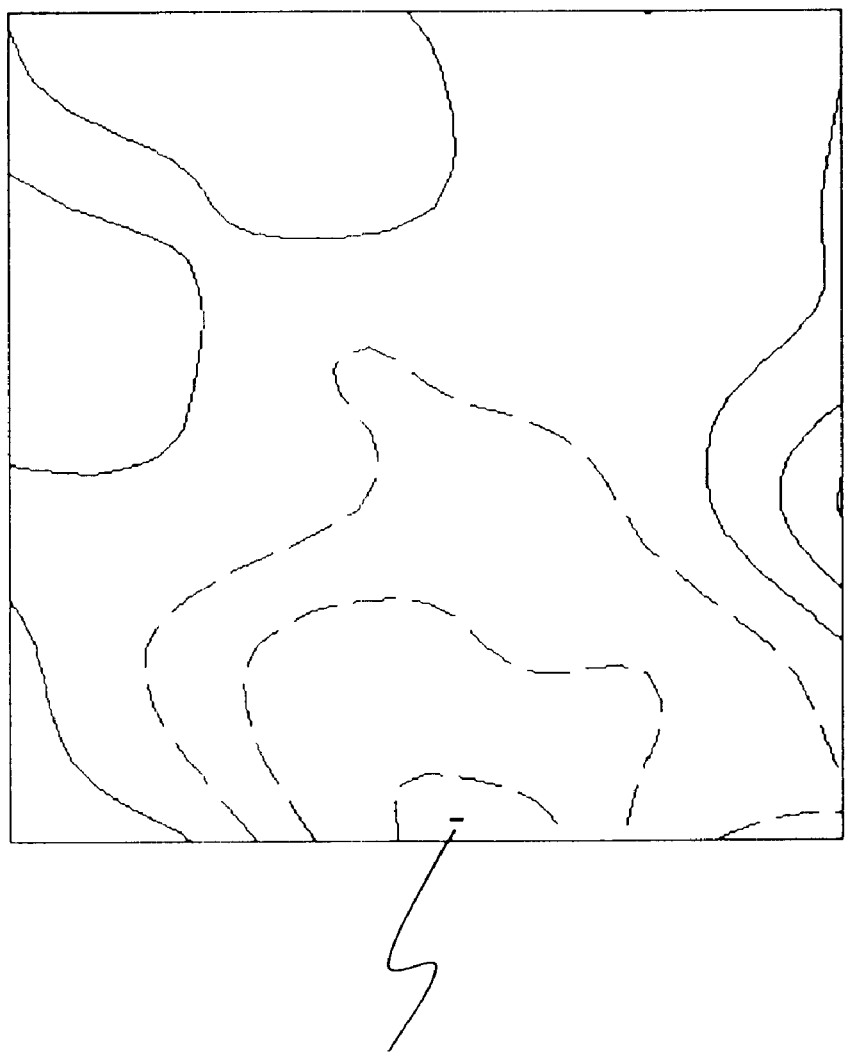
FIG. 9 is a map diagram based on rotation current arrows of a patient with dizziness.

For the purpose of evaluating quantitatively the rotation current arrow pattern, having the rotational property, of a patient with dizziness shown in FIG. 8, similarly to the case of FIG. 6, the rotation current arrow (Irot) was calculated. FIG. 9 shows a map diagram of the rotation current arrow (Irot) calculated from the current-arrow map shown in FIG. 8. Though in the case of FIG. 9, a negative peak 801 remarkably appears on the low side of the figure, a positive peak is hardly observed. Since in the present case of dizziness, the negative peak appears, it is conceivable that the counterclockwise rotation is generated.

Figure 10:
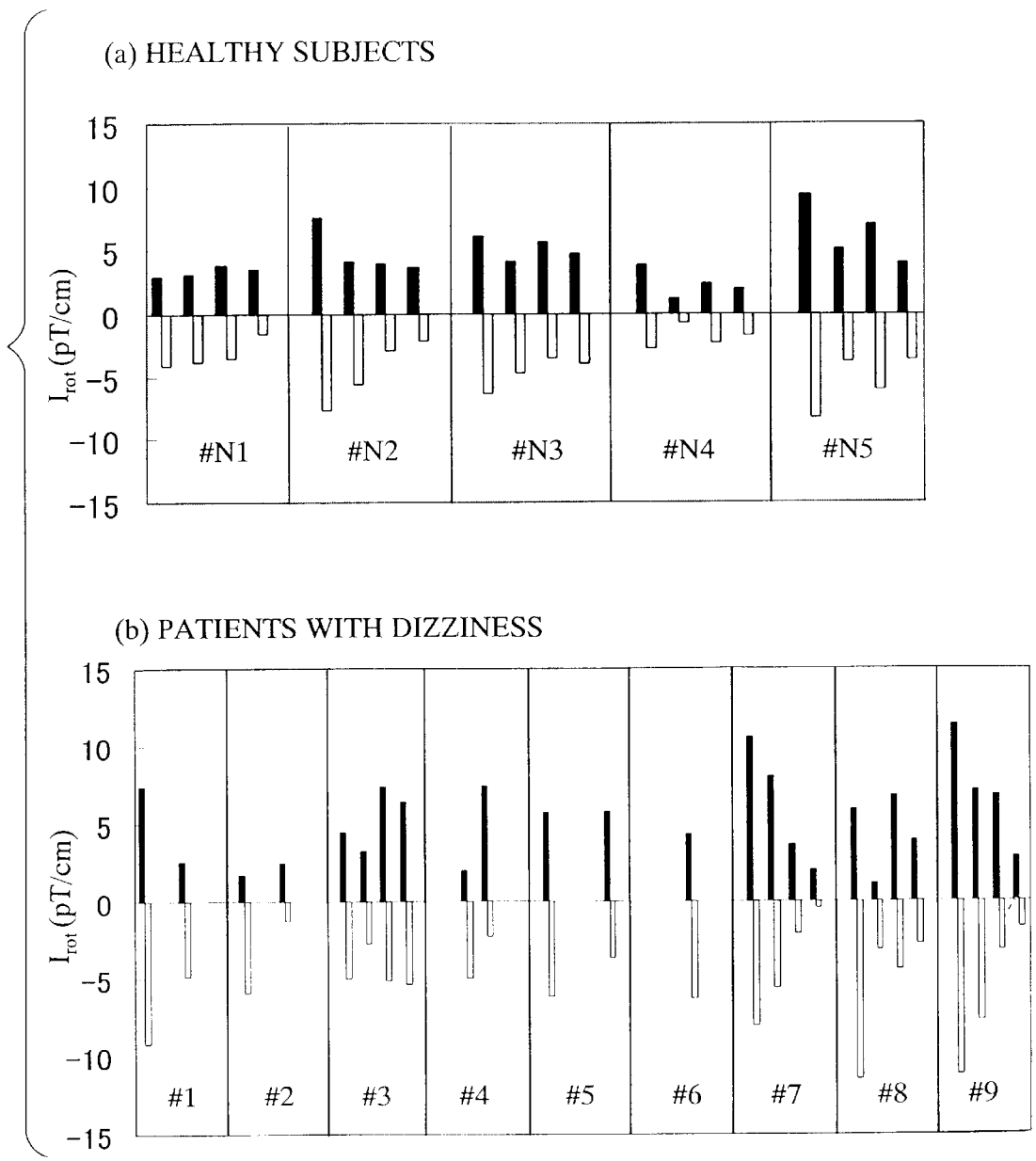
FIG. 10 is a graphical representation useful in explaining the comparison between healthy subjects and patients with dizziness with respect to a maximum value and a minimum value of rotation current arrows.

As described above, we have discussed the rotation current arrow (Irot) as a method of evaluating the rotation of the current arrows. In order to evaluate quantitatively the rotations with respect to all of patients, a positive peak value and a negative peak value were measured every measurement of each of patients (four patterns of the left temporal head—right sound stimulation, the left temporal head—left sound stimulation, the right temporal head—left sound stimulation, and the right temporal head—right sound stimulation). The results of the measurement are shown in FIG. 10. FIG. 10(a) shows five examples of healthy subjects, and FIG. 10(b) shows nine examples of patients with dizziness. But, #9 shows the result after completion of the amyodamin medical treatment for a patient with dizziness designated with #8. The results for each of patients correspond to the four patterns of the left temporal head—right sound stimulation, the left temporal head—left sound stimulation, the right temporal head—left sound stimulation, and the right temporal head—right sound stimulation from the left-hand side. Since in FIG. 10(a) for healthy subjects, with respect to each of subjects tested, the value on the positive side is roughly equal to that on the negative side, it is conceivable that the symmetric property is excellent. On the other hand, in the case of patients with dizziness shown in FIG. 10(b), there are the measurement parts in each of which N100 is not observed, and in addition thereto, it is understood that with respect to each of the measurement parts as well in each of which N100 is observed, there is shown the pattern having poor symmetric property in which the value on the positive side is different from that on the negative side.

Figure 11:
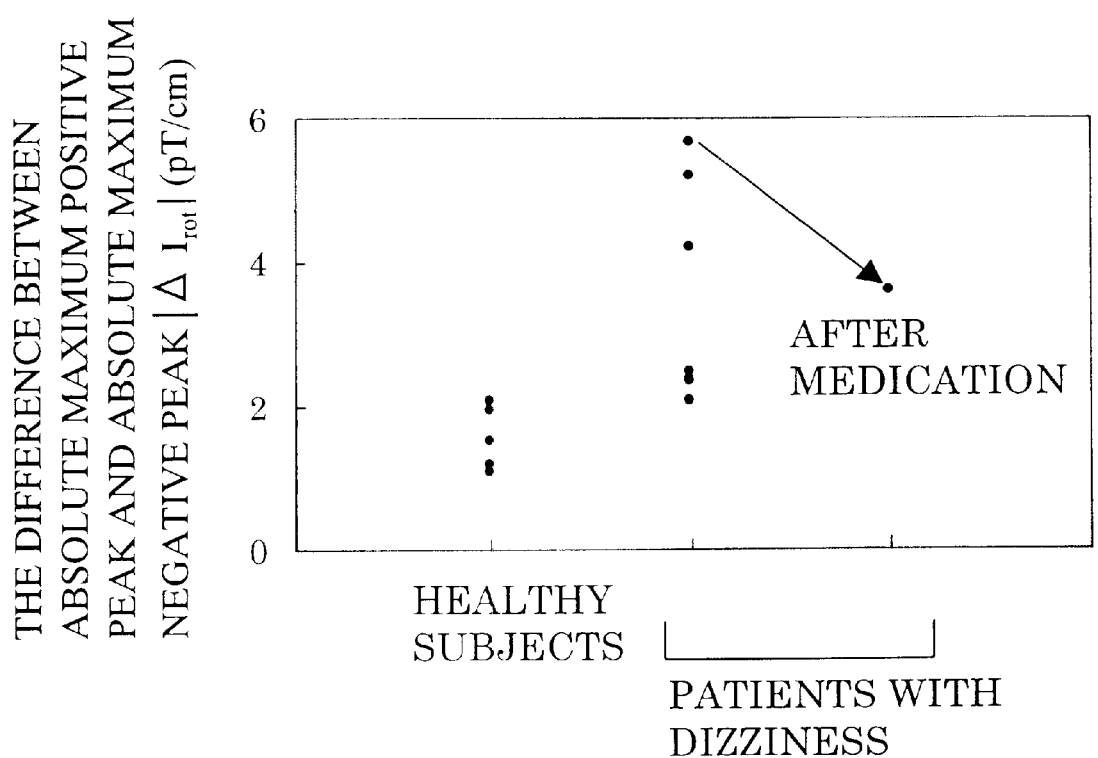
FIG. 11 is graphical representation useful in explaining the comparison between healthy subjects and patients with dizziness with respect to an absolute value of ((a positive side value) (a negative side value)).

In order to make the results shown in FIG. 10 clearer, the absolute value of (the value on the positive side)–(the value on the negative side) is calculated and the maximum values of the absolute values for each of subjects tested are compared with one another. As a result, as shown in FIG. 11, it can be made clear that there is the remarkable difference between healthy subjects and patients with dizziness. In addition, it was made clear that after giving a dose of the drug Merislon for suppression of dizziness to patients with dizziness, the maximum values are changed to the values near the maximum values for healthy subjects, and hence the dizziness symptoms is relaxed.

While in all of the embodiments as described above, an example of patients with dizziness in the measurement of the magnetoencephalogram has been shown, it is to be understood that the above-mentioned rotation current arrow (Irot) method is not intended to be limited to patients with dizziness, and thus the same rotation current arrow (Irot) can be calculated in even the heart disease, having a rotating current, in patients with atrial flutter, and hence it is possible to obtain the information useful in the quantitative evaluation for the heart disease.

It should be further understood by those skilled in the art that the foregoing description has been made on embodiments of the invention and that various changes and modifications may be made in the invention without departing from the spirit of the invention and the scope of the appended claims.

What is claimed is:

1. A biomagnetic field measuring apparatus for evaluating a rotational property of a current in a subject to be tested, comprising:

a bed for holding the subject to be tested;

a plurality of pickup coils arranged with respect to a measurement part of the subject;

superconducting quantum interference devices for converting a biomagnetic field detected by said pickup coils into electric signals;

a cryostat for holding said superconducting quantum interference devices at a low temperature;

means for holding said cryostat;

an operating circuit for driving said superconducting quantum interference devices;

means for acquiring and analyzing signals, as a measured biomagnetic field, due to a magnetic flux detected by said superconducting quantum interference devices;

display means for displaying analysis results obtained by said means for analyzing;

wherein said means for analyzing calculates a current arrow at measurement positions of the measured biomagnetic field by partially differentiating the measured biomagnetic field, and discretely curvilinearly integrates a tangential component of the current arrow contacting a circumference which is at an arbitrary distance from each of the measurement positions so as to obtain an integrated value for each of the measurement positions; and wherein said display means displays the integrated values.

2. A biomagnetic field measuring apparatus for evaluating a rotational property of a current in a subject to be tested, comprising:

a bed for holding the subject to be tested;

a plurality of magnetometers for measuring a normal component of a biomagnetic field generated from the subject be tested;

a cryostat for holding the plurality of magnetometers at a low temperature;

means for holding said cryostat;

a driving circuit for driving the plurality of magnetometers;

an arithmetic operation unit for collecting output signals from said driving circuit as a measured biomagnetic field and for operating arithmetically on the measured biomagnetic field; and display means for displaying a result obtained by said arithmetic operation unit;

wherein said arithmetic operation unit calculates current arrows at measurement positions of the measured biomagnetic field by partially differentiating the measured biomagnetic field, discretely curvilinearly integrates a tangential component of the current arrow contacting a circumference which is at an arbitrary distance from each of the measurement positions so as to obtain an integrated value for each of the measurement positions, and calculates a map diagram which is obtained by contour lines each connecting equal integrated values; and wherein said display means displays said map diagram.

3. A biomagnetic field measuring apparatus for evaluating a rotational property of a current in a subject to be tested, comprising:

a bed for holding the subject to be tested;

a plurality of magnetometers for measuring a normal component of a biomagnetic field generated from the subject be tested;

a cryostat for holding the plurality of magnetometers at a low temperature;

means for holding said cryostat;

a driving circuit for driving the plurality of magnetometers;

an arithmetic operation unit for collecting output signals from said driving circuit as a measured biomagnetic field and for operating arithmetically on the measured biomagnetic field; and display means for displaying a result obtained by said arithmetic operation unit;

wherein said arithmetic operation unit calculates current arrows at measurement positions of the measured biomagnetic field by partially differentiating the measured biomagnetic field, discretely curvilinearly integrates a tangential component of the current arrow contacting a circumference which is at an arbitrary distance from each of the measurement positions so as to obtain an integrated value for each of the measurement positions, calculates a minimum value and a maximum value of the integrated values, and calculates a difference value between the absolute value of said minimum value and said maximum value; and wherein said display means displays at least one of said minimum value, said maximum value and said difference value.

* * * * *